United States Patent [19]

Roberts

[11] 4,384,570

[45] May 24, 1983

[54] LARYNGOSCOPE

[76] Inventor: James T. Roberts, 901 Charles River St., Needham, Mass. 02192

[21] Appl. No.: 57

[22] Filed: Jan. 2, 1979

[51] Int. Cl.³ .............................................. A61B 1/00
[52] U.S. Cl. .................................................... 128/4
[58] Field of Search ..................................... 128/3–6, 128/9–20, 208, 351

[56] References Cited

U.S. PATENT DOCUMENTS

| | | | |
|---|---|---|---|
| 2,435,400 | 2/1948 | Long | 128/11 |
| 2,630,114 | 3/1953 | Hart | 128/11 |
| 2,646,037 | 7/1953 | Cook et al. | 128/6 |
| 3,888,117 | 6/1975 | Lewis | 128/20 X |
| 4,050,466 | 9/1977 | Koerbacher | 128/208 X |
| 4,086,919 | 5/1978 | Bullard | 128/11 |

FOREIGN PATENT DOCUMENTS 2353223 4/1975 Fed. Rep. of Germany ........ 128/10

OTHER PUBLICATIONS

Ring et al., "A New Device for Exposure of the Oropharynx", *Arch. Otolaryng.*, vol. 96, (Jul. 1972).

*Primary Examiner*—John D. Yasko
*Attorney, Agent, or Firm*—Paul J. Cook

[57] ABSTRACT

A laryngoscope including a blade and a handle having a rigid handle section and a movable handle section is disclosed. The movable handle section is adapted to be pivoted and locked at a desired position relative to the rigid section prior to use with a patient.

8 Claims, 5 Drawing Figures

LARYNGOSCOPE

BACKGROUND OF THE INVENTION

This invention relates to a therapeutic instrument known as a laryngoscope used to visualize the laryngeal area of the human body.

Laryngoscopes are routinely used to facilitate endotracheal intubation such as during surgery to permit the patient to breathe and/or to administer anesthesia. In addition, laryngoscopes are utilized to displace the tongue and epiglottis thereby to permit direct visualization of the glottis through the mouth opening.

The standard method for performing intubation involves placing the patient in a supine position, tilting the head backwards as far as possible and distending the lower jaw to open the mouth widely. A rigid blade, which can be straight or slightly curved, then is inserted through the mouth into the throat passageway to displace the tongue and epiglottis thereby to expose the glottis. Thereafter, the desired visual observation can be achieved, the anesthetic can be applied and/or the mechanical ventilation may be effected. When utilized, the endotracheal tube is inserted either orally or transnasally and passed along the laryngoscope blade into the glottis.

Endotracheal intubation performed in the foregoing manner may cause undesirable physiological reflexes and require the use of an anesthetic. The use of such blades frequently requires contact with the upper teeth so that the blade is pivoted about the edge of these teeth during use. This frequently results in the teeth being broken or injured. In addition, the size and shape of the tracheal passage varies with the patient, particularly, if the patient is afflicted with a disease that affects the trachea. Thus, with a laryngoscope having a rigid blade of fixed size and shape, possible injury to the patient is increased as the size and shape of the trachea varies from patient to patient. Although transnasal intubation minimizes the possible injury to teeth during endotracheal intubation, it has certain disadvantages. The reverse curve of the passage used to enter the larynx and trachea from the nose is difficult to traverse safely with conventional endoscopes due to their limited degree of distal articulation. Accordingly, it would be desirable to provide a means for effecting endotracheal intubation which minimizes or eliminates the drawbacks associated with conventional laryngoscopes and which are more convenient to use than presently available nasopharyngoscopes.

SUMMARY OF THE INVENTION

The present invention provides a laryngoscope having a blade and a handle, a section of which is pivotally mounted so that the user of the laryngoscope can position himself to apply a force on the blade in a manner such that little or no force is directed onto the upper teeth. Since the blade is pivotally mounted, the laryngoscope can be utilized easily by right-handed or left-handed persons. The laryngoscope also can be provided with means for adjusting the blade angle and/or length to accommodate different patients with one instrument. Furthermore, the laryngoscope can be provided with fiber optic means to afford passage of light into the trachea for viewing by the person using the laryngoscope. Furthermore, the laryngoscope can be provided with a means for delivering anesthesia into the trachea of the patient. Also, the laryngoscope can be provided with an alarm means which alerts the user to accidental application of pressure to the upper teeth during use.

DETAILED DESCRIPTION OF SPECIFIC EMBODIMENTS

The essential feature of the present invention is a handle for a laryngoscope, a section of which is pivotally mounted so that the angle of its position with respect to the blade section of the laryngoscope can be changed to accommodate any user of the laryngoscope and to permit application of force onto the blade without applying force to the upper teeth of the patient. Since the handle section which is pivotally mounted is sufficiently large for the user to grasp it, the force applied by the user to the laryngoscope is concentrated at the axis of the pivot point of the pivotally mounted handle section rather than at the juncture of the handle and the blade which is located adjacent the teeth of the patient when the laryngoscope is in use. By constructing the laryngoscope in this manner, greatly improved safety to the patient during use is provided.

Figure 1:
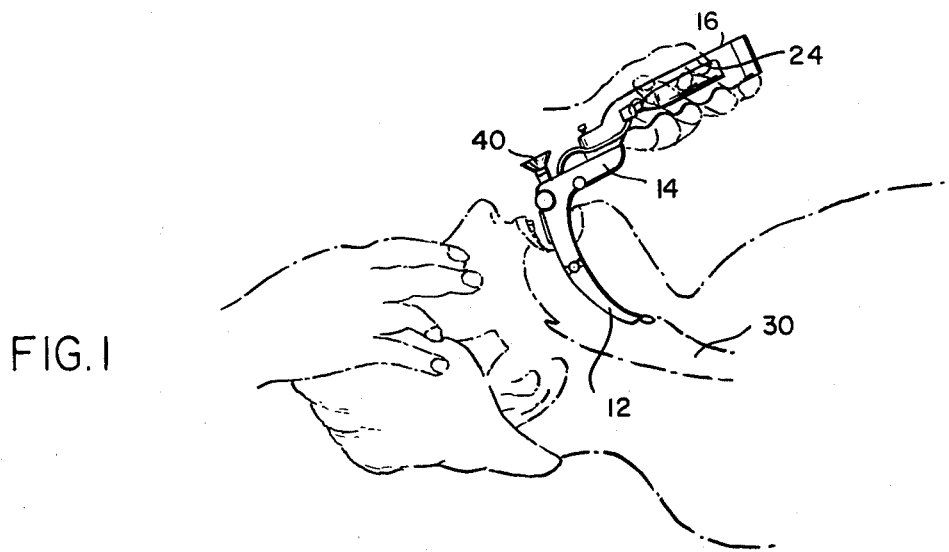
FIG. 1 shows the laryngoscope of this invention in use.
Figure 2:
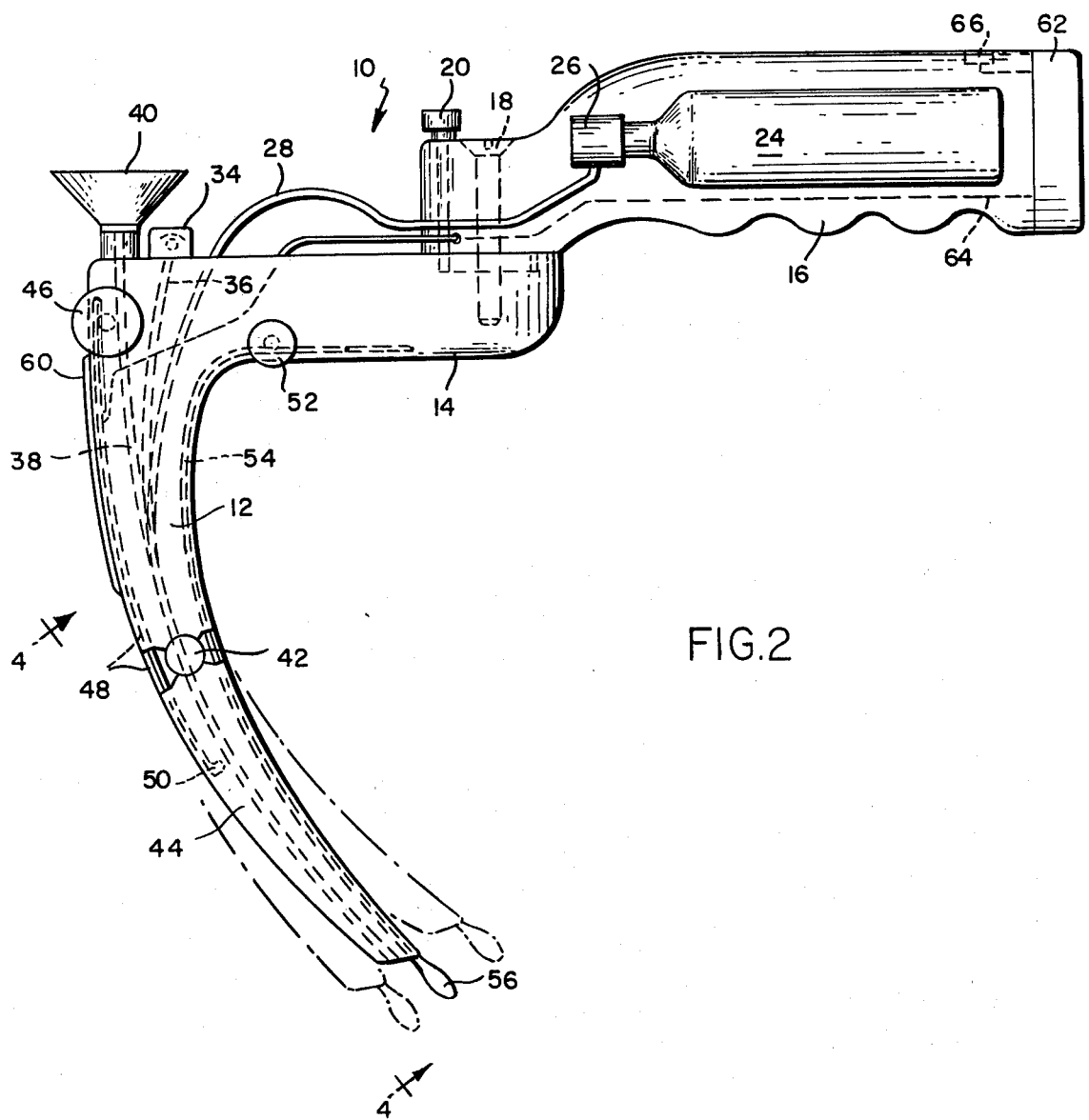
FIG. 2 is a side-view of the laryngoscope of this invention.
Figure 3:
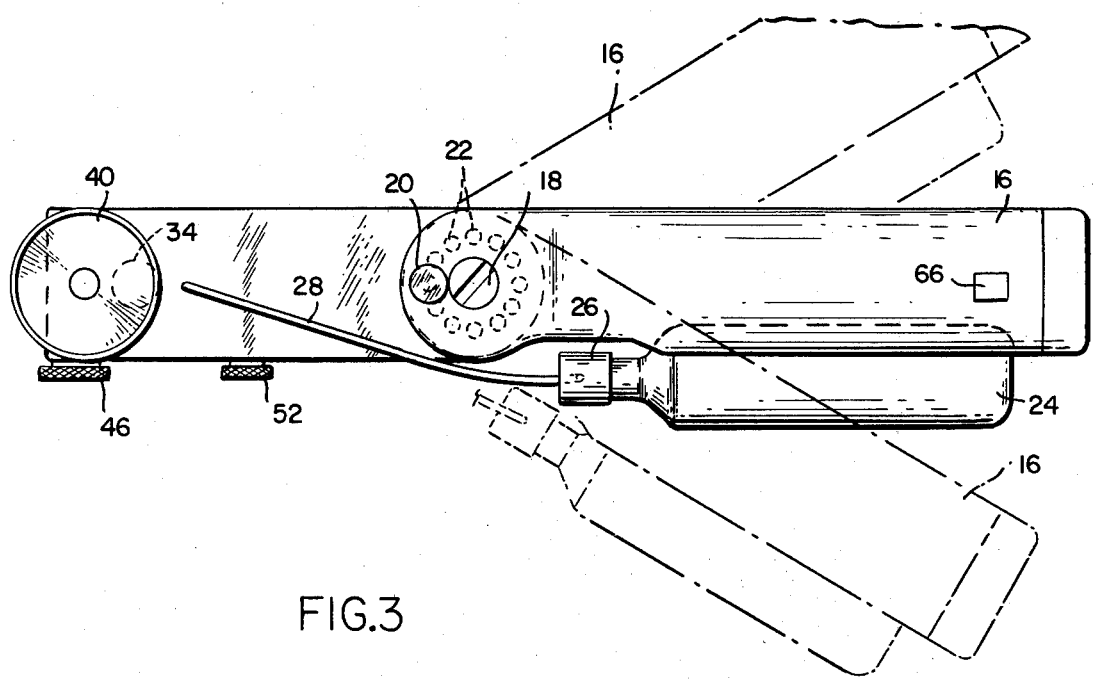
FIG. 3 shows the adjustable handle of the laryngoscope of this invention.

The present invention will be described in detail with reference to the accompanying drawings. As shown in FIGS. 1 and 2, the laryngoscope 10 includes a blade section 12 and a handle section comprising a fixed handle section 14 and a pivotally mounted handle section 16. The handle section 16 is adapted to be contiguous with handle section 14 and is pivotally mounted on screw 18. The position of handle section 16 is fixed by means of locking pin 20 which fits into one of a plurality of slots 22 (also see FIG. 3). Thus, the handle section 16 can be positioned at a plurality of angles with respect to the blade 12 in a 360° circumference (also see FIG. 3). A container 24 for an anesthetic is mounted on handle 16 in any convenient manner such as by being adhered to the handle section 16. The container 24 is provided with an aspirator 26 which is connected to tube 28 which extends through the blade section 12 so that an anesthetic can be delivered into the patient trachea 30 during use. The laryngoscope 10 also can be provided with fiber optic means which includes a light source 34, a fiber optic bundle 36 which extends to the end of the blade section 12 for delivery of light into the trachea 30. In addition, a second fiber optic bundle 38 is provided for passing the light reflected from the trachea back up through the blade section 12 to the viewer 40 thereby permitting viewing of the trachea during use of the laryngoscope 10.

Figure 4:
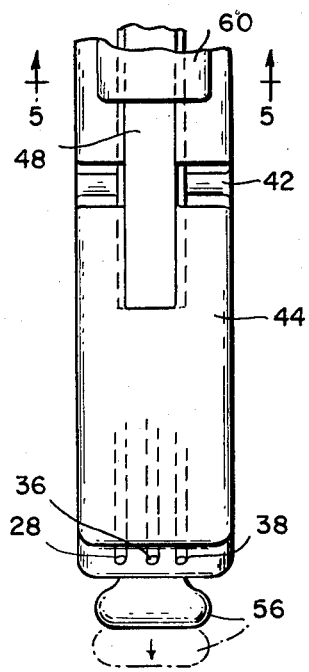
FIG. 4 is a side-view of the blade section of the laryngoscope of FIG. 2.
Figure 5:
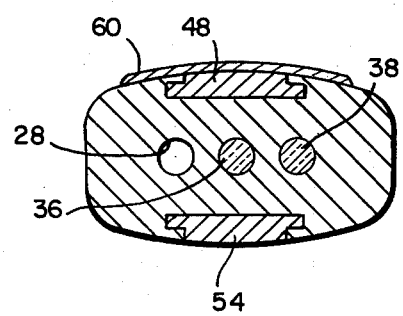
FIG. 5 is a cross-sectional view of the laryngoscope shown in FIG. 4 taken along lines 5—5.

As shown in FIGS. 2 and 4, the blade section 12 also is pivotally mounted about pivot 42 so that the angle of the lower blade section 44 can be adjusted within the oral pharynx by means of a ratchet 46 which adjusts the length of the metal band 48, the end of 50 of which is secured to lower blade section 44. (See FIG. 2.) The laryngoscope 10 is also provided with a means for extending the effective length of the laryngoscope by means of ratchet 52 which is associated with metal band 54 that is attached to the tip 56 of the laryngoscope. By adjusting the length of the band 54 between the ratchet 52 and the tip 56, the effective length of the laryngoscope also can be adjusted. (See FIG. 4.) Finally, the laryngoscope can also be provided with a safety means to alert the user when undue pressure is being applied to the upper teeth. The safety means comprises a pressure plate 60 that is electrically connected to a battery 62 in handle section 16 by means of wire 64 so that when undue pressure is applied to pressure plate 60 adjacent the upper teeth of the patient, an electrical signal is transmitted to a light or buzzer 66 positioned within handle section 16.

What I now claim is:

1. A laryngoscope for endotracheal intubation comprising an elongated blade shaped to fit into the oral pharynx of a patient and a handle, said handle comprising a rigid handle section attached to one end of said blade and a movable handle section pivotally mounted to said rigid handle section and adapted to pivot about an axis being both substantially perpendicular to the length of said rigid handle section and extending in substantially the same direction as the length of said blade and means for locking said movable handle section during use of said laryngoscope.

2. The laryngoscope of claim 1 including means for adjusting the length of said blade.

3. The laryngoscope of claims 1 or 2 including means for adjusting the angle of said blade.

4. The laryngoscope of claims 1 or 2 including means connected to said handle for delivering an anesthetic to the trachea of a patient when the distal end of said blade is inserted into said trachea.

5. The larynogoscope of claims 1 or 2 including means for delivering light to the trachea of a patient when the distal end of said blade is inserted into said trachea and means for viewing said delivered light reflected from the trachea.

6. The laryngoscope of claim 3 including means connected to said handle for delivering an anesthetic to the trachea of a patient when the distal end of said blade is inserted into said trachea.

7. The laryngoscope of claim 3 including means for delivering light to the trachea of a patient when the distal end of said blade is inserted into said trachea and means for viewing said delivered light reflected from the trachea.

8. The laryngoscope of claim 4 including means connected to said handle for delivering an anesthetic to the trachea of a patient when the distal end of said blade is inserted into said trachea.

* * * * *